US008065167B1

(12) United States Patent
Wyman

(10) Patent No.: US 8,065,167 B1
(45) Date of Patent: Nov. 22, 2011

(54) COMPUTER SYSTEMS FOR MANAGING PATIENT DISCHARGE

(76) Inventor: Robert Kurt Wyman, Dana Point, CA (US)

( * ) Notice: Subject to any disclaimer, the term of this patent is extended or adjusted under 35 U.S.C. 154(b) by 271 days.

(21) Appl. No.: 12/463,232

(22) Filed: May 8, 2009

Related U.S. Application Data

(60) Provisional application No. 61/052,126, filed on May 9, 2008.

(51) Int. Cl.
  *G06Q 50/00* (2006.01)
(52) U.S. Cl. .................................... 705/3; 705/2
(58) Field of Classification Search ................ 705/2, 3
  See application file for complete search history.

(56) References Cited

U.S. PATENT DOCUMENTS

| | | | |
|---|---|---|---|
| 5,301,105 | A | 4/1994 | Cummings, Jr. |
| 7,711,579 | B2 * | 5/2010 | Lancaster et al. ................ 705/2 |
| 7,734,477 | B2 * | 6/2010 | Bellin et al. ..................... 705/2 |
| 2004/0128168 | A1 * | 7/2004 | Wyatt ............................... 705/2 |
| 2005/0075544 | A1 * | 4/2005 | Shapiro et al. ................ 600/300 |
| 2007/0142713 | A1 | 6/2007 | Lancaster et al. |
| 2007/0214011 | A1 | 9/2007 | Demers |
| 2009/0164236 | A1 * | 6/2009 | Gounares et al. ................ 705/2 |

FOREIGN PATENT DOCUMENTS

WO  WO-97/50050  * 12/1997

* cited by examiner

*Primary Examiner* — Gerald J. O'Connor
*Assistant Examiner* — Teresa Woods
(74) *Attorney, Agent, or Firm* — Knobbe Martens Olson & Bear LLP

(57) ABSTRACT

A system for electronically managing patient discharges may include a patient data repository that can store patient data. The system may also include a provider repository that can store medical provider data having information about one or more providers of services to discharged patients. Moreover, the system may include a discharge planning module that can output a discharge planning user interface for presentation to a user. The discharge user interface can have functionality for the user to input post-discharge medical care options for a medical patient. The discharge planning module can also access the provider data in the provider data repository in response to receiving the post-discharge medical care options from the user, select medical providers from the provider data who have characteristics in the provider data that match the medical care options, and electronically send a discharge request to the selected medical providers.

3 Claims, 23 Drawing Sheets

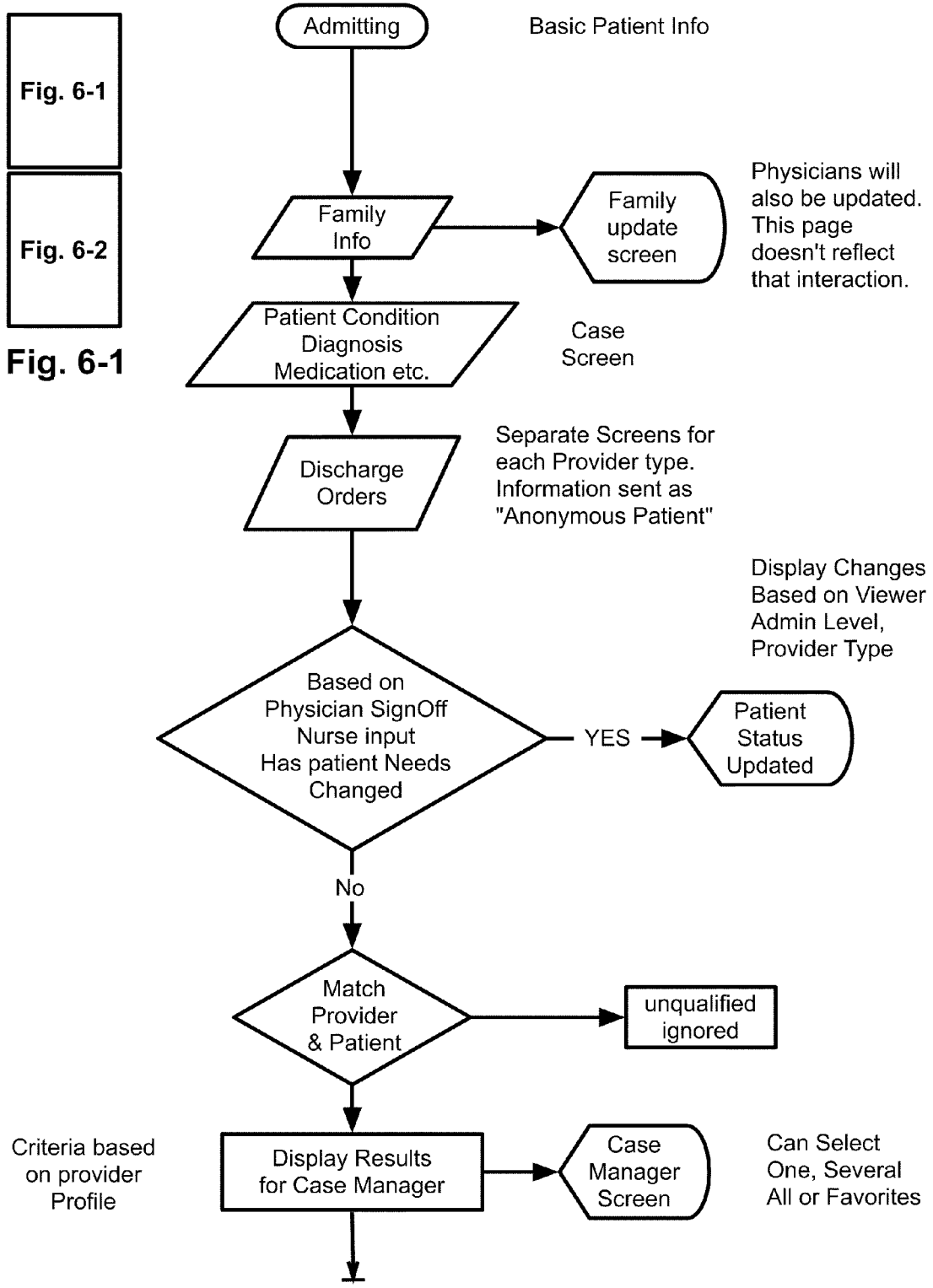

Patient Fulfillment Screen

Patient info | Medical Equip | HomeHealth & Hospice | Pharmacy | Medical Transport Diagnostic Services | Registry | Extended Care Facilities | Therapy & Treatment Services

| Patient Fulfillment Screen | Product & Service Library |
|---|---|
| Provider Logo<br><br>Patient: Patient's Name<br>Hospital Room # ___  Bed # ___<br>SSN ___<br>Discharge: 1:PM  Nov  28  2005<br>Requested Provider Response Time: 3HRs<br>Medical Equipment<br>Fulfilled: Click Field for Provider INFO<br>Items: Wheel Chair / Oxygen / C-PAP<br>Home Health & Hospice<br>Waiting: Romona VNA<br>Waiting: Vistas<br>Declined: Home Care Assistance<br>Pharmacy<br>Fulfilled: Sav-on #23671-00983<br>Medical Transportation<br>- Private Auto<br>Diagnostic Services<br>- • Not Requested •<br>Extended Care<br>- • Not Requested •<br>Extended Care<br>Fulfilled: X-Ray -• Zoo Labs at 2:PM<br>Fulfilled: CT-Scan -• L&L Medical @ 4:PM<br><br>(Reset) | Ad or Product Graphic<br><br>Ad or Product Graphic<br><br>Ad or Product Graphic<br><br>Ad or Product Graphic<br><br>Ad or Product Graphic<br><br>Ad or Product Graphic<br><br>Library Information |

Fig. 7

Provider Logo

Hospital Room # ☐   Bed # ☐
Medical Rcrd # ☐

200 Patient Information

| | |
|---|---|
| Patient Name | ☐ |
| Patient DOB | Month ☐  Day ☐  ☐ Year |
| Age | ☐ Years    Sex ☐ |
| Veteran | ☐ |
| Maritial Status | ☐ |
| Racel Ethnicity | ☐ |
| Height | ☐ Inches |
| Weight | ☐ lbs |
| SSN | ☐ ☐ ☐ |
| Address | ☐ |
| City | ☐ |
| Zip | ☐ |
| | ☐ ☐ ☐  CA ☐ |

| Fig. 8-1 |
|---|
| Fig. 8-2 |
| Fig. 8-3 |

Fig. 8-1

210 Advance Directive option to send directive to doctors or extended care facilities Restrictions ☐ DNR   ☐ DNI   ☐ Feeding   ☐ Meds
Other ☐ Living Will   ☐ Organ Donor   ☐ ATPS

220 Family or Patient Advocate

Name [Optional - More Names can be added]
Phone ☐ ☐ ☐

Option to add more family - normally 3 members are listed - nice to include an order of preference. Also ability to put in several phone numbers per person.
(cell, home, work, other)

| | | |
|---|---|---|
| 230 | Scheduled Discharge Time | |
| | | Time ⇕  Month ⇕  Day ⇕  Year ⇕ |
| | Provider Response Time | 1 Hour ⇕ |
| 240 | Vitals | Patient is stable<br>Pulse is 76<br>systolic 110 to 150 |
| | Diagnosis | CD-9 Codes here<br>HCPCS |
| | Diagnosis Hx | 01/16/2005 Well Adult<br>01/09/2005 Viral Syndrome |
| | Wounds | Severe Diabetic Foot Ulcers |
| | Routine Medications | Diovan 80 mg<br>Glucophange xr |
| | Prescription Hx | 01/16/2005 Lipitor 10 mgi<br>1/16/2005 Glucophage Xr |
| | Procedure Hx | 01/16/2005 DT<br>12/21/2004 Ear Irrigation |
| | Test List | 08/12/2004 HDL cholesterol<br>08/12/2004 LDL cholestrol |
| | Allergy List | Codeine |
| | Other Sensitivities | Erythromycin causes Nausea |
| | FmHx | HTN 401.9<br>Fdied of MI age 48 |
| | pHx \| PmHx | HTN 401.9<br>DM, Adult Onset, NID, Control |
| | Social Hx | Unrestrained Driving<br>Tobacco Use 1-2 ppd |
| | Chart Notes | |
| | Insurance #1 | United Health Care<br>Group: Retired Teachers Association |
| | Insurance #2 | |

Fig. 8-2

250 Physician [                    ] Add Physician

☐ Rx Approved

260 Case Manager [            ]
Phone [        ] ext [    ]
Case Date [        ]
Case Manager Notes [ notes are optional ]

( Reset )  ( Submit )
( Alert Providers to Patient update )

Fig. 8-3

Provider Logo

400   Patient [Patient's Name]
     SSN [ ]     [select another patient]

410   AMBULATORY AIDS
- ☐ Cane    ☐ Crutches
- ☐ Walker

Comments Additional Explain [ ]

420   BATHROOM AIDS
- ☐ Commode    ☐ Toilet Seat
- ☐ Shower Chair    ☐ Shower Bench
- ☐ Grab Bar Comments Additional Explain [ ]

430   OTHER SPECIALITY DME
- ☐ Hoyer Lift    ☐ Trapeze
- ☐ Lift Chair    ☐ Over Bed Table Comments Additional Explain [ ]

440   WHEELCHAIR SCOOTERS

[Wheel Chair - Scooters ▼]

WHEELCHAIR ACCESSORIES
- ☐ Gel Cushion
- ☐ Elevated Leg rest
- ☐ Oxygen Tank Holder Comments Additional Explain [ ]

450   RESPIRATORY EQUIPMENT
- ☐ RT Requested
- ☐ Oxygen Concentrator    ☐ Portable System
- ☐ Portable Conserving Sys    ☐ IPPB/IPV
- ☐ CPAP/BPAP    ☐ Suction
- ☐ Ventilator    ☐ Aerosol Compressor
- ☐ Nebulizer Compressor Comments Additional Explain [ ]

RESPIRATORY ACCESSORIES
- ☐ Peak Flow Meter    ☐ Trach Care Kit
- ☐ Incentive Spirometer    ☐ Ambu Bag
- ☐ Heated Humidifer    ☐ Aero Chamber
- ☐ Cool Humidifer Comments Additional Explain [ ]

[Reset] [Submit]

[Alert Providers to Patient update]

Fig. 9

Provider Logo

500 Patient [Patient's Name]
SSN [ ]   [select another patient]

510 Select HomeHealth
- ☐ Romona VNA
- ☐ Vitas
- ☐ Hospice of the Valley
- ☐ Home Instead
- ☐ Home Care Assistance
- ☐ All point Report Card
Report Card
Report Card 550
Report Card
Report Card
Report Card

520 ☐ Home Health

530 ☐ Hospice

540 ☐ Private Duty Nurse (Care Giver)

Comments Additional Explain [ ]

(Reset) (Submit)
(Alert Providers to Patient update)

Fig. 10

Provider Logo

Patient: Patient's Name

SSN:

Choose Pharmacy

☐ Sav-on                Report Card
☐ Rite-Aid              Report Card
☐ Bear Creek Pharmacy   Report Card Instructions ☐ Patient Pickup        ☐ Delivery Requested Medication:

Prescriptions:

Comments
Additional
Explain:

( Reset )  ( Submit )

( Alert Providers to Patient update )

Fig. 11

Provider Logo

Patient [Patient's Name]
SSN [ ]

Select Service Provider
- ☐ DME Diagnostics — Report Card
- ☐ Loma Linda Sleep Lab — Report Card
- ☐ Shiva Heart Center — Report Card
- ☐ UNI-Lab — Report Card
- ☐ Lab — Report Card
- ☐ Lab — Report Card Diagnostic Services
- ☐ Pulse Oximetry Study    ☐ Rest    ☐ Exert
- ☐ Overnight Pulse Oximetry Study
- ☐ Sleep Apnea Screening (4 Channel)
- ☐ Complete Sleep Study
- ☐ Basic Spirometry
- ☐ Pulmonary Function Test

- ☐ CT Scan
- ☐ X-Ray
- ☐ MRI
- ☐ Nuclear Scan

- ☐ Stress Treadmill
- ☐ Stress Echo
- ☐ EKG
- ☐ Holter Monitoring

- ☐ Lab

Test [test]

Comments Additional Explain [notes are optional ->]

(Reset) (Submit)
(Alert Providers to Patient update)

Fig. 12

| Provider Logo |
|---|

Patient [Patient's Name]
SSN [Patient's Name]

Select Assisted Living Facility
- ☐ Sterling — ! VACANCY
- ☐ Chancellor — ! VACANCY
- ☐ Wildomar — NO Vacancy
- ☐ Country Villa — NO Vacancy
- ☐ Pleasant Care — Report Card Select Skilled Nursing Facilities
- ☐ Victoria — ! VACANCY
- ☐ Alamitos-Belmont — ! VACANCY
- ☐ Chase Care Center — NO Vacancy Comments Additional Explain [                    ]

( Reset )  ( Submit )

( Alert Providers to Patient update )

COMPUTER SYSTEMS FOR MANAGING PATIENT DISCHARGE

RELATED APPLICATIONS

This application claims the benefit of priority under 35 U.S.C. §119(e) of U.S. Provisional Patent Application No. 61/052,126, filed on May 9, 2008, entitled "Computer Systems for Managing Patient Discharge," the disclosure of which is hereby incorporated by reference in its entirety.

BACKGROUND

In order to discharge patients from hospitals or other clinical facilities, a great deal of planning often takes place. A care worker assigned as a discharge planner typically begins the discharge process on the day the patient enters the hospital. The discharge planner prepares a significant amount of paperwork to ensure that discharged patients receive proper, safe medical care upon leaving the clinical facility. This post-discharge medical care can be provided by medical providers such as skilled nursing facilities (SNFs), assisted living centers, pharmacies, medical equipment providers, medical transport (e.g., ambulances), therapy and treatment centers (e.g., dialysis treatment), medical laboratories, and the like.

In order to ensure a safe discharge for a patient, a discharge planner typically faxes discharge requests, which include large amounts of patient information, to several medical providers. The discharge planner then waits for a response from the medical providers. Each medical provider reviews the extensive fax documents to find relevant information about the patient and then determines, depending on the type of medical provider, if a room, medicine, equipment, therapy, or the like is available for the patient. The medical providers then fax back their responses, and the discharge planner chooses from among the medical providers who responded positively.

SUMMARY

A system for electronically managing patient discharges may include a patient data repository that can store patient data. The system may also include a provider repository that can store medical provider data having information about one or more providers of services to discharged patients. Moreover, the system may include a discharge planning module that can output a discharge planning user interface for presentation to a user. The discharge user interface can have functionality for the user to input post-discharge medical care options for a medical patient. The discharge planning module can also access the provider data in the provider data repository in response to receiving the post-discharge medical care options from the user, programmatically and/or automatically select medical providers from the provider data who have characteristics in the provider data that match the medical care options, and electronically send a discharge request to the selected medical providers.

For purposes of summarizing the disclosure, certain aspects, advantages and novel features of the inventions have been described herein. It is to be understood that not necessarily all such advantages may be achieved in accordance with any particular embodiment of the inventions disclosed herein. Thus, the inventions disclosed herein may be embodied or carried out in a manner that achieves or optimizes one advantage or group of advantages as taught herein without necessarily achieving other advantages as may be taught or suggested herein.

BRIEF DESCRIPTION OF THE DRAWINGS

Throughout the drawings, reference numbers may be re-used to indicate correspondence between referenced elements. The drawings are provided to illustrate embodiments of the inventions described herein and not to limit the scope thereof.

FIG. 7 illustrates an example patient fulfillment screen that may be provided by the discharge planning system of FIG. 1 or 2;

FIG. 8 illustrates an example patient input screen that may be provided by the discharge planning system of FIG. 1 or 2;

FIG. 9 illustrates an example provider display for durable medical equipment that may be provided by the discharge planning system of FIG. 1 or 2;

FIG. 10 illustrates an example provider display for home health and hospice care that may be provided by the discharge planning system of FIG. 1 or 2;

FIG. 11 illustrates an example provider display for pharmacy services that may be provided by the discharge planning system of FIG. 1 or 2;

FIG. 12 illustrates an example provider display for diagnostic services that may be performed by the discharge planning system of FIG. 1 or 2;

FIG. 13 illustrates an example provider display for extended care that may be provided by the discharge planning system of FIG. 1 or 2;

DETAILED DESCRIPTION

Introduction

The process of faxing patient information to medical providers and waiting for responses can be inefficient and time-consuming. In addition, faxing patient information can be insecure, as a misdialed fax number can send sensitive patient information to unintended recipients. This disclosure therefore describes systems and methods for managing patient discharge, which in certain embodiments can advantageously simplify and enhance the security of the discharge process.

Figure 1:
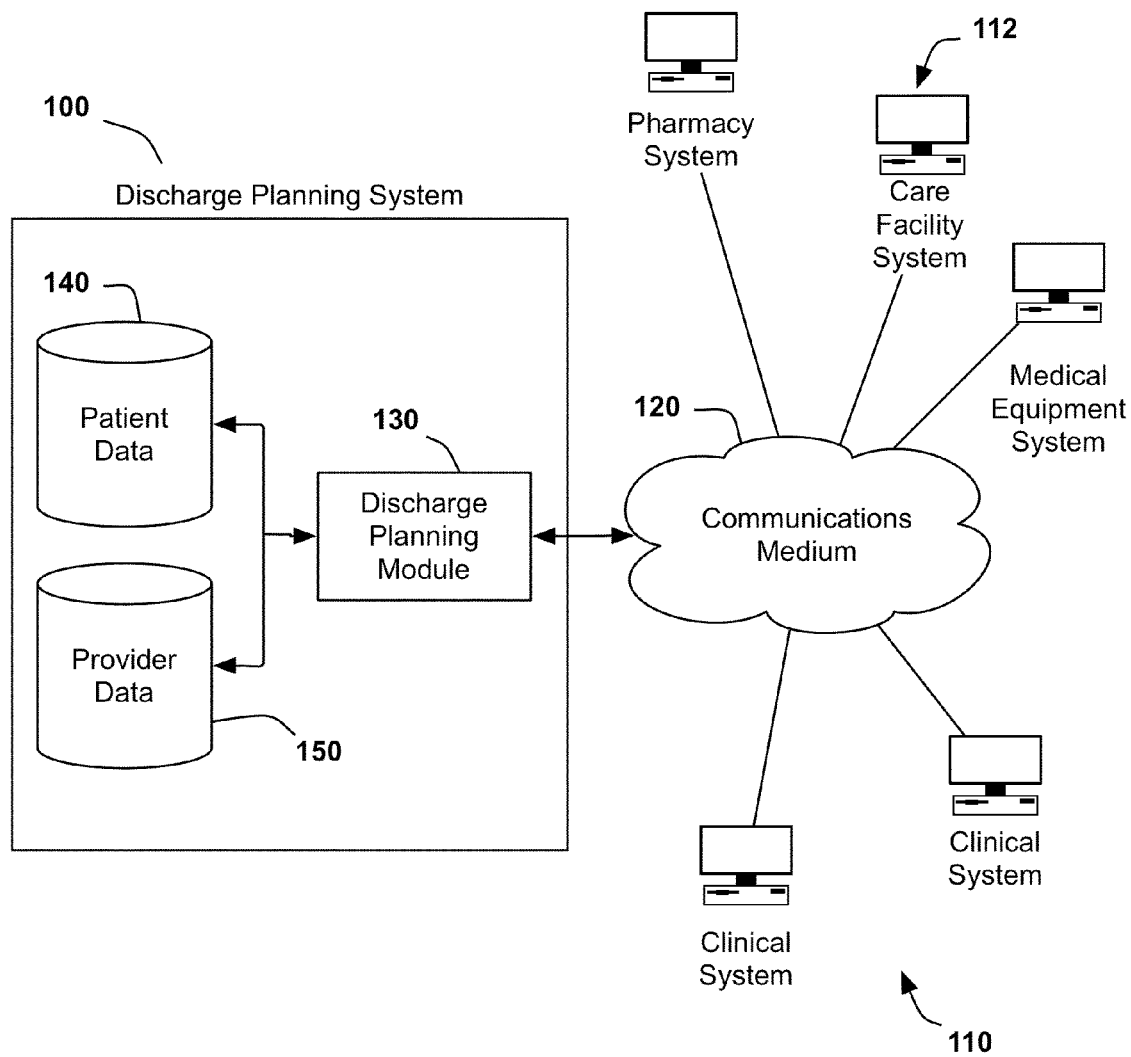
FIG. 1 illustrates an embodiment of a discharge planning system.

Referring to FIG. 1, an embodiment of a discharge planning system 100 is shown. In certain embodiments, the discharge planning system 100 enables more efficient and secure discharge planning. The discharge planning system 100 may be hosted by an application service provider (ASP) in certain embodiments. As such, the discharge planning system 100 may be accessed by a plurality of clinical facilities, which may include hospitals, skilled nursing facilities, assisted living centers, extended care facilities, and any other medical facility that discharges patients.

In the depicted embodiment, two clinical systems 110 are in communication with the discharge planning system 100. Each of the clinical systems 110 is a computer system, such as a desktop computer, laptop computer, personal digital assistant (PDA), tablet computer, smart phone, combinations of the same, and the like. Each of the clinical systems 110 can represent a computer system of a discharge planner at a clinical facility. Two clinical systems 110 are shown, representing two clinical facilities. In various implementations, multiple clinical systems 110 can be used at a single clinical facility.

The clinical systems 110 communicate with the discharge planning system 100 over a communications medium 120, which may be a network such as the Internet or the like. In an embodiment, the communications system 120 is a peer-to-peer network. By using a peer-to-peer network as opposed to a server-based network, in certain embodiments the communications medium 120 can be more secure.

In addition to the clinical systems 110, medical providers 112 are in communication with the discharge planning system 100. These medical providers 112 may include pharmacies, care facilities (e.g., skilled nursing, assisted living, extended care, laboratories, and the like), medical equipment vendors, medical transport (e.g., ambulances), treatment centers (e.g., for dialysis treatment or physical therapy) and the like. Each of the medical providers 112 can include one or more computer systems for interacting with the discharge planning system 100. Example computer systems are shown. In certain embodiments, these computer systems may include desktop computers, laptop computers, personal digital assistants (PDA), tablet computers, smart phones, combinations of the same, and the like.

In certain embodiments, the discharge planning system 100 includes a discharge planning module 130. The discharge planning module 130 can be an application, an application server (hardware or software), or the like that enables a discharge planner using a clinical system 110 to manage patient discharge. In one embodiment, the discharge planning module 130 generates a user interface to enable discharge planners using the clinical system 110 to plan patient discharges. The user interface may include one or more web pages or other network resources that may be accessed by the clinical system 110 using a web browser or the like. In other embodiments, an application or thick client (not shown) installed on the clinical system 110 may generate some or all of the user interface.

Using the user interface on a clinical system 110, a discharge planner may provide patient information to the discharge planning module 130. This patient information can include, for example, biographical data (e.g., name, address, social security number, and the like), health status, medications used by the patient, medical conditions of the patient, medical devices required by the patient, diagnoses, prognoses, patient insurance information, physician(s) of the patient, medical history of the patient, combinations of the same, and the like. In an embodiment, the discharge planning module 130 stores this patient information as patient data 140. The patient data 140 may be stored in one or more storage repositories, databases, file systems, or the like. Over time, the clinical system 110 may send patient information updates to the discharge planning module 130, which may store the updates in the patient data 140.

In one embodiment, the patient data 140 is stored in two databases to enhance security. A first database can include all of the patients' data 140 except some or all of the patients' biographical data. For example, this first database may not include the patients' names or other identifying information. Instead, an alias or other patient identifier may be linked with the patient data 140 for each patient. Thus, the patient data 140 in this first database can be anonymous. The second database may include the patients' names and/or other biographical data, associated with the patient identifiers from the first database. Thus, if the first database is compromised by a hacker or the like, the patients' identities may not be compromised.

The discharge planner can use the clinical system 110 to send discharge orders for patients to the discharge planning module 130. In certain embodiments, a discharge order can cause the discharge planning module 130 to initiate a discharge process. The discharge order may include a request for post-discharge medical care for the patient. A discharge planner may, for instance, enter this information into a form of the user interface and submit the form to the discharge planning module 130.

The discharge planning module 130 receives the discharge order, and in certain embodiments, accesses provider data 150 to make a preliminary determination as to which medical providers 112 match the patient's needs. The provider data 150 can include information on the medical providers 112. For example, this information might include data on the closest care facilities to the hospital, rates for the care facilities, levels of care provided by the care facilities, insurances accepted, and so forth. The provider data 150 may be stored in one or more storage repositories, databases, file systems, or the like. This data 150 may be provided to the discharge planning module 130 by the medical providers 112.

Once the discharge planning module 130 has made a preliminary selection of medical providers 112 that may match the patient's needs, the discharge planning module 130 in certain embodiments sends a discharge request to the selected medical providers 112 over the communications medium 120. The discharge request can include, for example, a request for the patient to stay at a care facility upon discharge, a request for prescriptions to be filled upon discharge, a request for medical equipment to be provided, combinations of the same, and the like. In an embodiment, the discharge request can include some or all of the patient information for the patient. The discharge request in certain embodiments does not include the patient's biographical data, name, or the like to preserve patient anonymity. Instead, the discharge request can include the patient identifier described above. The discharge planning module 130 can communicate the discharge requests using encrypted or unencrypted email, HTML documents, other types of messages or documents, combinations of the same, or the like.

In turn, the medical providers 112 can respond by accepting or denying the discharge request. For example, a care facility can indicate its willingness to take the patient for extended care. As another example, an ambulance worker with a PDA or the like can receive the discharge request, determine if the ambulance is equipped to handle the patient, and send back an acceptance or denial to the discharge planning module 130. In an embodiment, the medical providers 112 can respond to the discharge requests using encrypted or unencrypted email, web documents, other types of messages or documents, combinations of the same, or the like. In another embodiment, a discharge request module (not shown) may be included on each of the medical providers' 112 systems, which may receive the discharge requests. The discharge request module can automatically process the request in certain embodiments. The discharge request module can alternatively be used by a user to process the discharge request.

Once the medical providers 112 have responded with acceptances or denials, the discharge planning module 130 can forward on the acceptances to the clinical system 110. Then, the discharge planner can choose one or more of the accepting medical providers 112 and communicate this choice or choices to the discharge planning module 130. The discharge planning module 130 can pass on the discharge planner's choice or choices to the medical provider(s) 112. In an embodiment, the discharge planning module 130 passes on the biographical information of the patient along with the discharge planner's choice or choices.

While the discharge planning system 100 is shown as hosted by an ASP in the depicted embodiment, in alternative embodiments a separate discharge planning system 100 may be installed on each clinical system 110 of each clinical facility. The clinical facilities may instead host their own discharge planning system 100, rather than using an ASP's hosting services. Additionally, the clinical facilities may have installed locally at least a portion of the functionality of the depicted discharge planning system 100 while accessing an ASP host for other features of the discharge planning system 100. The clinical facilities might, for example, access a discharge planning module 130 of the ASP host but store their own patient data 140 and/or provider data 150. Or, the clinical facilities might have a local copy of the discharge planning module 130 but use the ASP host to access or store patient data 140 and/or provider data 150. Moreover, in certain embodiments, the clinical systems 110 may have some of the functionality of the discharge planning module 130, while the ASP-hosted discharge planning system 100 has other functionality of the discharge planning module 130.

Additional Example Embodiments

Each of the embodiments described below may be implemented by the discharge planning system 100. In certain additional embodiments, systems and methods for managing patient discharge include an electronic system that uses a software application and internet connection to assist in patient discharge, transition, including scheduling for equipment supply, treatment and care.

Discharger Planner is a computer program that organizes the discharge process; it aids case managers by accessing a database of providers' abilities, providers' acceptance of insurances, and providers' schedules, which is used to interface each patient's needs and insurer. It serves as a communication terminal for providers and case managers to facilitate discharge. It offers many features that improve administrative control and oversight over this area of patient care.

The program can allow case managers to locate and communicate with providers who can provide services and products to the patients who need them. Real Time communication and updates keep length of stay schedules on track. Up-front filtering of provider's ability to accept insurance speed up the decision process and reduce delays in patient discharge.

All these features generally do not require upfront software or hardware purchases. Rather, in certain embodiments, these features may be used on a pay per use wireless, fully web or internet based system.

In certain embodiments, benefits may include:
1. Improved patient-hospital relationships.
2. Improved accuracy in equipment and service selection.
3. Faster access to product information.
4. Better patient and family involvement, may improve JCAHO scores.
5. HMO case managers can instantly and remotely connect to patients in your hospital, easily update and review patient status, diagnosis, and discharge time.

Thus, in certain embodiments, a software/system/procedure is provided that in certain embodiments can simplify the communication process between care facilities, healthcare services, diagnostic services, pharmacy, transport and medical equipment providers.

A software/system/procedure is provided in certain embodiments that can securely transmit patient information like age, height, weight, sex, address, phone condition diagnosis, treatment, insurance information, using a secure HIPAA compliant internet connection. At the "push of a button" this automated system may match the post hospital care needs of a patient with the providers' ability to fulfill an order and accept insurance. This eliminates or reduces the need to manually fax requests or make phone calls to each provider in certain embodiments. In some cases, this beneficially reduces or eliminates the tendency to find and use a single provider for multiple equipment needs.

Once the patient needs have been identified and the appropriate insurance and diagnostic information has been entered, a single "click" may be performed to have this system begin the process of selection, notification, and follow up. A status screen can be accessed at any time to monitor the fulfillment process and the case manager/social worker/discharge planner/provider will be notified if a problem is anticipated.

The system can quickly match patient insurance with provider acceptance. Automation in provider selection reduces or eliminates, in certain embodiments, unnecessary calling and faxing, which may result in improved discharge time and cost efficiency.

The system may also securely and instantly connect with providers such as but not limited to:
Medical Equipment (DME)
Home Health
Hospice
Pharmacy
Medical Transport
Extended Care Facilities
Therapy and Treatment When there are changes made to patient condition, diagnosis, or discharge time, providers are automatically updated in certain embodiments.

Fulfillment screens may allow case managers to know who has reviewed patient information without the need for a provider to personally confirm notice. Through the fulfillment screen, providers can communicate in a wide variety of means including email, text messages, and/or fulfillment screens if providers accept or decline. Profiles may allow case managers to select various methods of communication. Profiles can be updated at any time. Case Managers/Discharge Planners/Providers can also use the fulfillment screen to log phone calls, make notes, add comments, or memos associated with each discharge. Notes can be shared or private.

Case manager's fulfillment screens provide updated information on each case instantly including a list of providers, equipment, and services. This information is available through a laptop computer, PDA, smart phone, or other wireless device, or any computing device. Reviewing a complete list of patient's discharge status will save time, improving efficiency. Supervisors can quickly review cases and case management remotely or locally.

Information is tracked and the system may includes reporting capabilities. Quick reports include discharge status, LOS, even bed availably. Administrators and Supervisors can create custom queries on discharge data. Reported data can include patient demographic information, such as age, sex, county of residence, diagnostic information, treatment information, and disposition.

Mandatory reporting like MIRcal reports can be created from system data. Administrators have oversight capabilities and can set required reporting fields, services, and medical equipment based on status and diagnosis or treatment. Administration controls include: reporting, queries, procedures, and planning.

Case managers can retrieve information about products and services to help plan the discharge and fulfill a patient's requirements, and maintain length of stay schedule. Case managers can easily find product information, facility information, and services provided by SNF, Assisted Living, DME, Transport, and Treatment centers.

Providers can make 'real time' updates to their available products and services including making changes to which insurance they accept or no longer accept or are contracted with.

Protection of patient information may be achieved with a software application (e.g., a client) that uses the internet, with or without the aid of a browser. A direct connection may be established between this client and the application server. The application server recognizes only the client request for communication in certain embodiments.

Alerts to physicians, providers, and hospitals can also be done through traditional means like email, Text Messages, Fax or Phone Messaging. These alerts may contain no patient information, just basic information to create an alert or update.

The starting point for most communication can be to input patient information. One scenario would be the hospital setting. A patient is admitted the case manager inputs patient name, address, phone, insurance, family members to contact, physician, condition. The system can immediately begin to match this information to a provider's ability to accept and fulfill patient's needs.

Once the insurance information becomes part of the patient record, the system can match all providers who accept that insurance. The system continues to match by location, condition, diagnosis, treatment, requirements for care, medication, equipment and services. Each provider is then matched against patient needs. Providers selected are displayed for approval by discharge planners. Providers can be individually contacted or a broadcast contact can be made to all qualifying providers. Responses from providers are displayed and case managers can assign the case, or partial case to any provider.

In certain embodiments, this substantially improves the existing system of communication between hospitals and providers, hospitals and physicians, providers to other providers. Currently available systems require many faxed pages to be sent for each communication, which is a slow and tedious process that is sometimes faulty.

Figure 2:
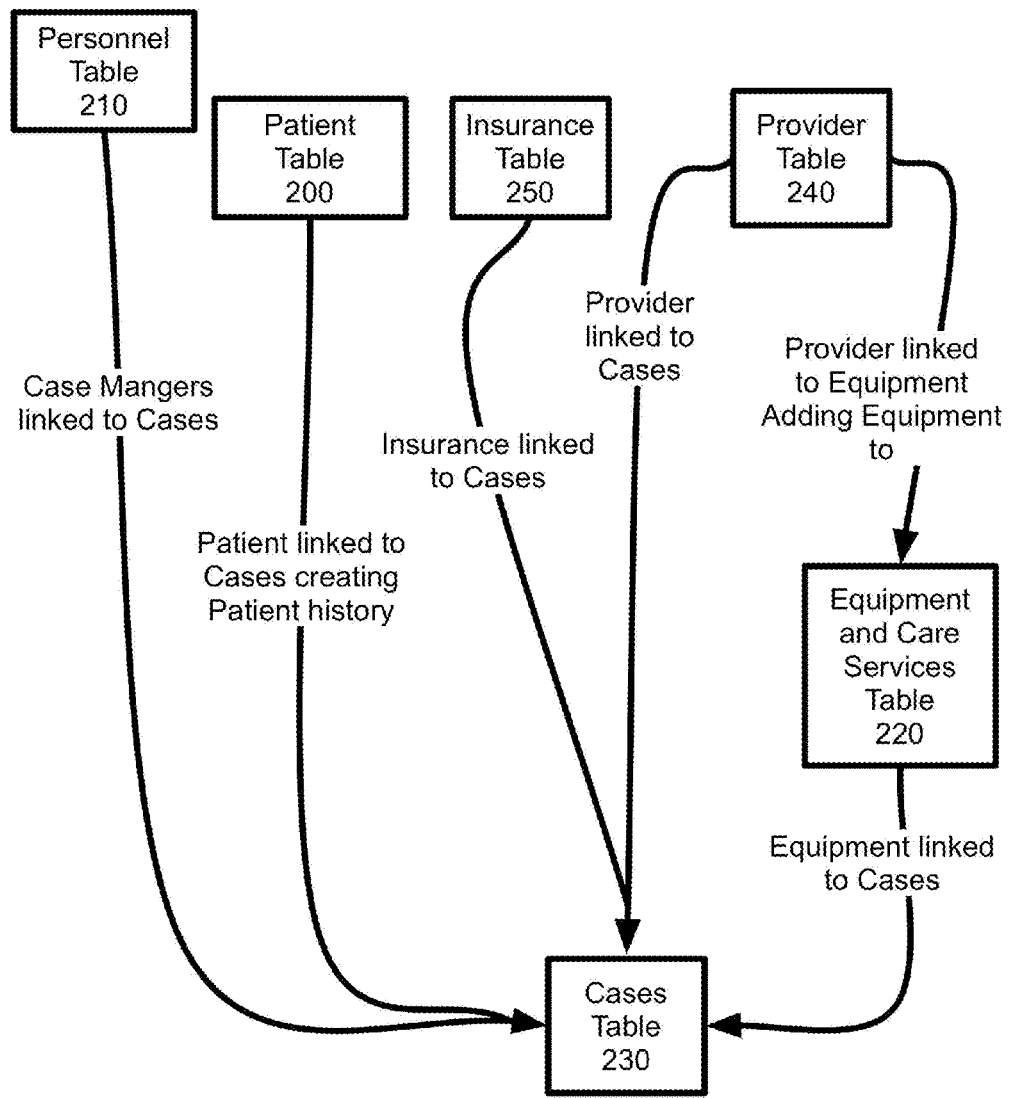
FIG. 2 illustrates an example database schema usable with the discharge planning system of FIG. 1.

Referring to FIG. 2, an example database schema usable with the discharge planning system 100 is shown. The database schema includes the following items are shown: Patient table [200]—This holds the patient data that does not change. Name (maiden name), Birthdate, Sex, SSN. Case Manager table [210]—(the Personnel table). Holds some or all providers or personnel including physicians including private practice, administrators, nurses, case managers, discharge planners. Moreover, it holds the personnel who may have access at the provider level, giving admin control to some or all providers over employee access to system. Equipment Category table [220]—. This table combines an Equipment list table and a Provider items table. It holds some or all Medical Equipment, some or all Care Services, some or all Facility Information, some or all Pharmaceutical supplies & drugs, some or all Treatments offered, some or all Therapies offered, Care facilities and hospitals w/bed inventory, Diagnostic services can inventory available time. Some or all things a patient needs may be within this table. Case History detail table [230]. Each time a patient is setup on the Clinical System this opens up a new case. Within the case are some or all details of the patient current to the case.

Example: A patient's weight is stored in the Case file so weight history is available. It includes an Equipment usage table. Provider table [240]—Contains some or all providers, including hospitals and physicians. Insurance table [250]—Contains some or all Insurance companies.

Figure 3:
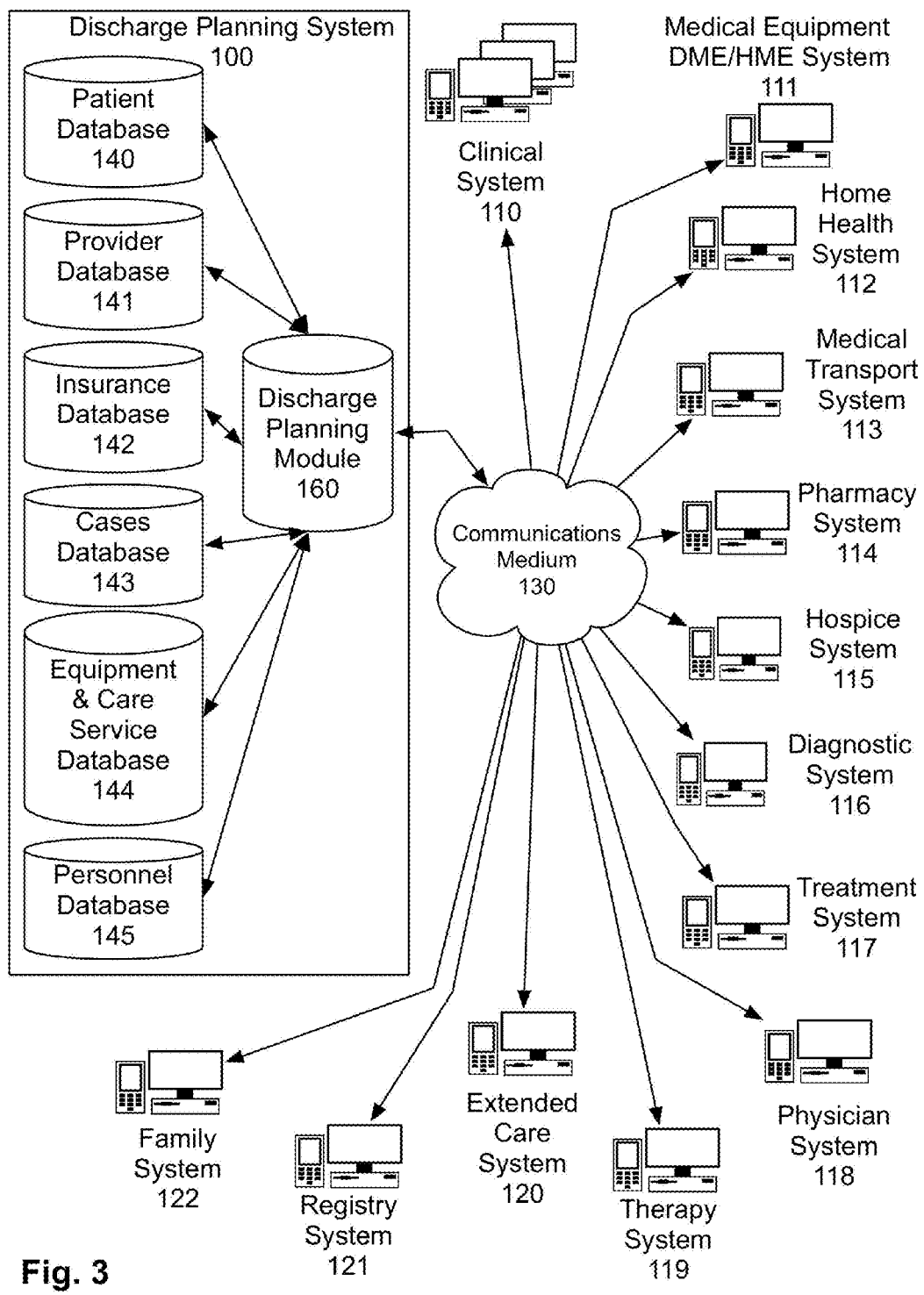
FIG. 3 illustrates a more detailed embodiment of the discharge planning system of FIG. 1.

FIG. 3 illustrates a more detailed embodiment of the discharge planning system 100 of FIG. 1. With respect to FIG. 3, the following items are shown: 100—Discharge Planning System; 110—Clinical System—Originator of Discharge—by example we use a hospital, but the system allows for any provider to discharge a patient using any other provider on the system to fulfill patient needs. Some or all Systems have the option to use Cell Phone, Smart Phone, iPhone, PDA access and/or alerts. 111—Medical Equipment Provider . . . DME Durable Medical Equipment, HME Home Medical Equipment. 112—Home Health Provider—Care provider Nursing, bathing, in home therapy and rehabilitation. 113—Medical Transport—Ambulance, Life Flight, Taxi, Family, Self. 114—Pharmacy—prescriptions, supplies. 115—Hospice—care facility, in home, at other facility. 116—Diagnostic—schedule, and patient handoff. 117—Treatment—schedule, and patient handoff. 118—Physician—Any physician. 119—Therapy—Therapy Providers. 120—Extended Care—Any physician. 121—Physician—Any physician. 122—Physician Any physician.

Figure 4:
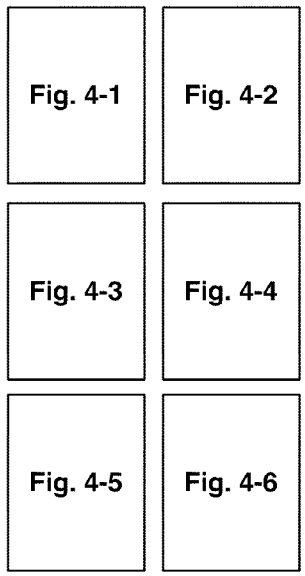
FIG. 4 illustrates an embodiment of a discharge planning process that may be performed by the discharge planning system of FIG. 1 or 2.
Figure 1:
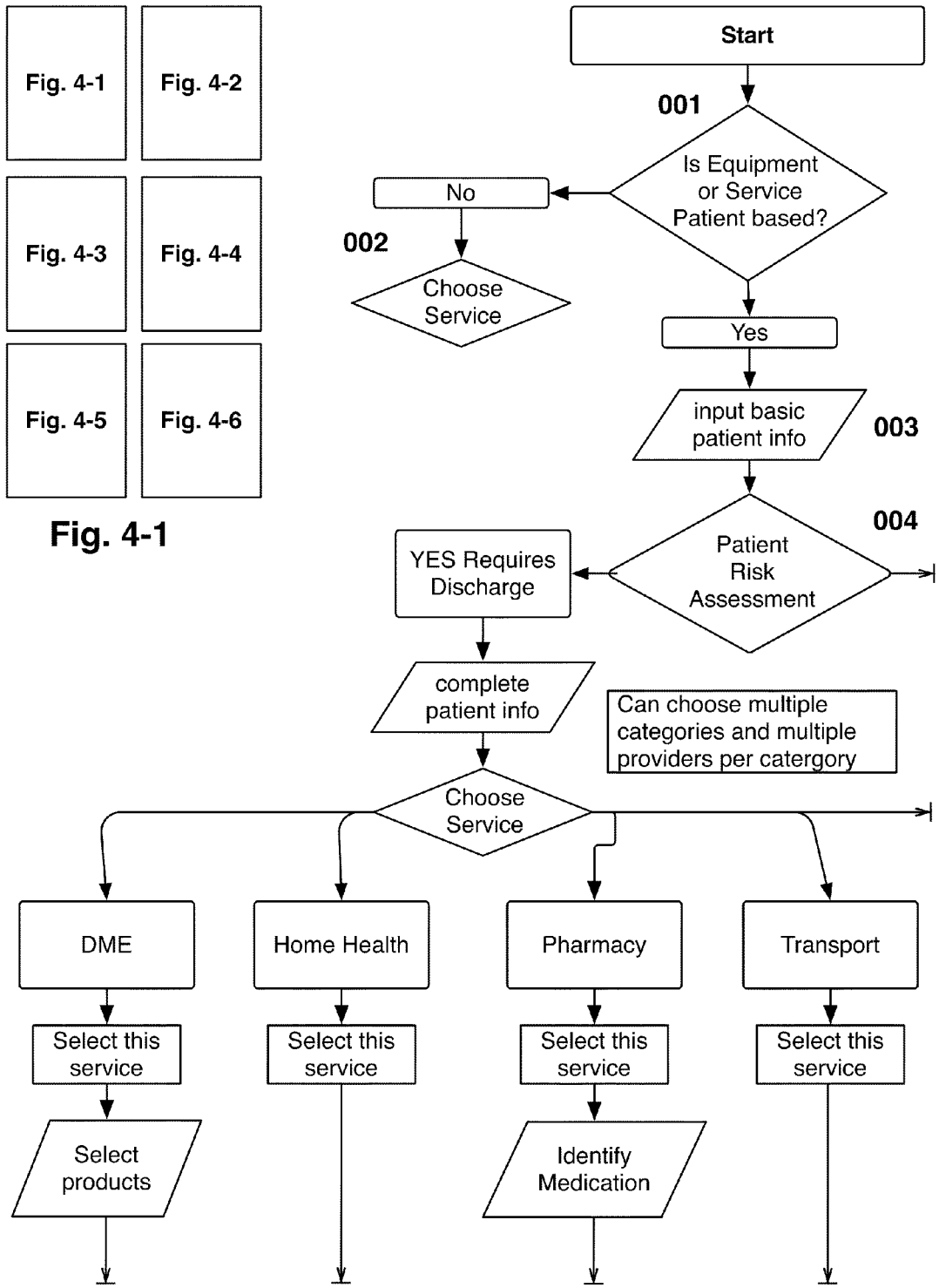
Figure 4:
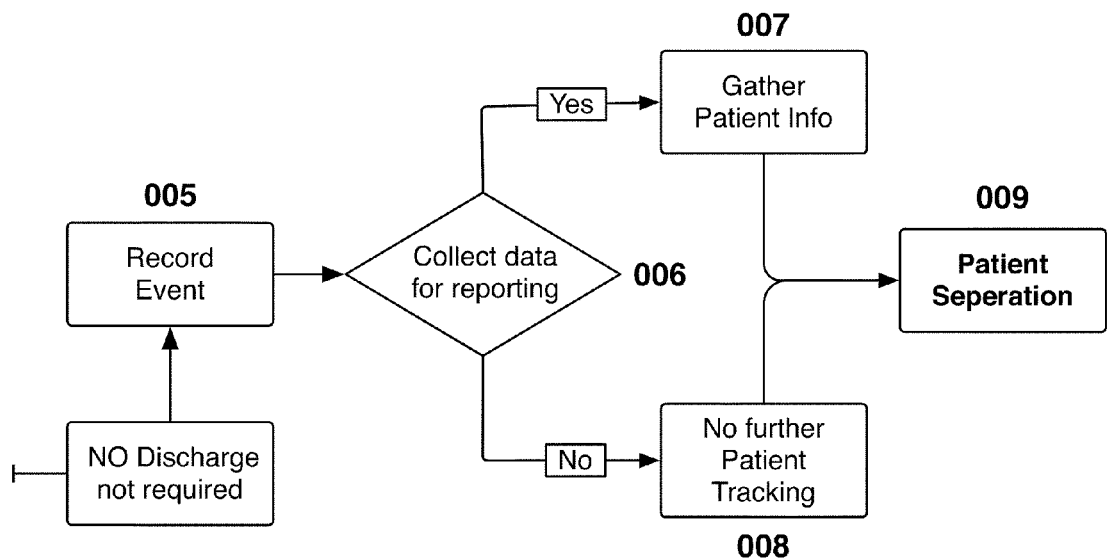
Figure 2:
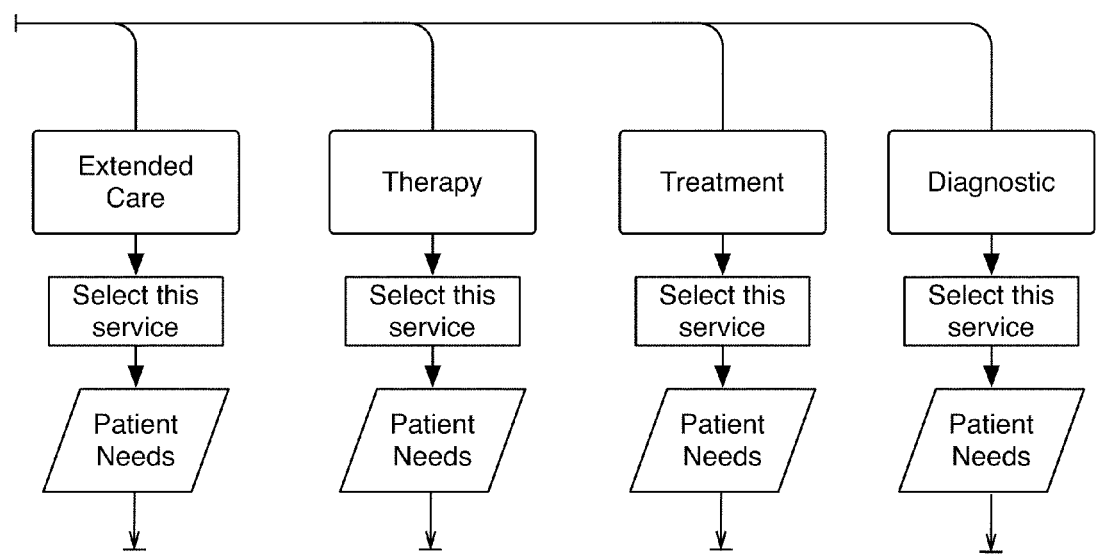
Figures 3, 4:
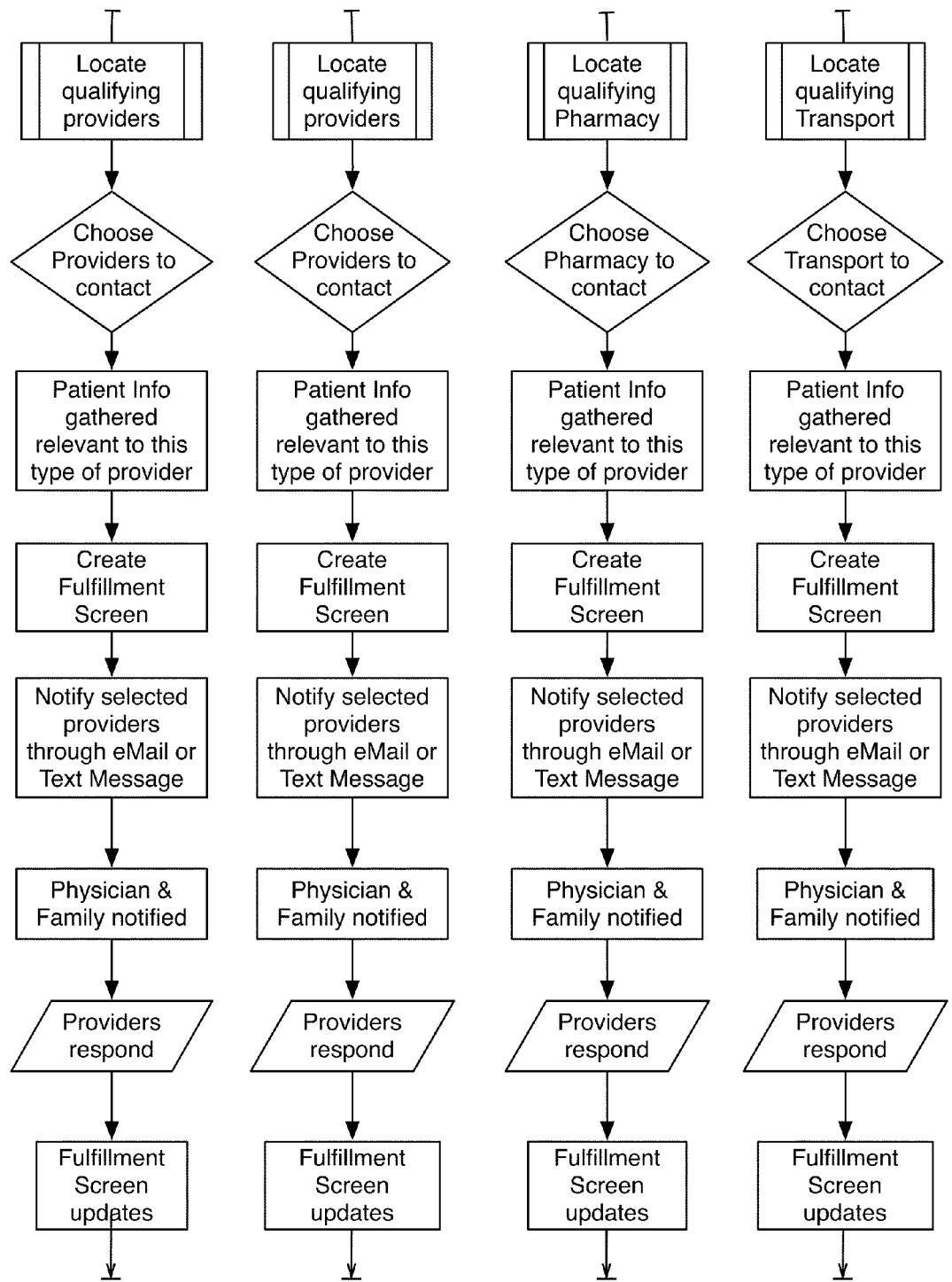
Figure 4:
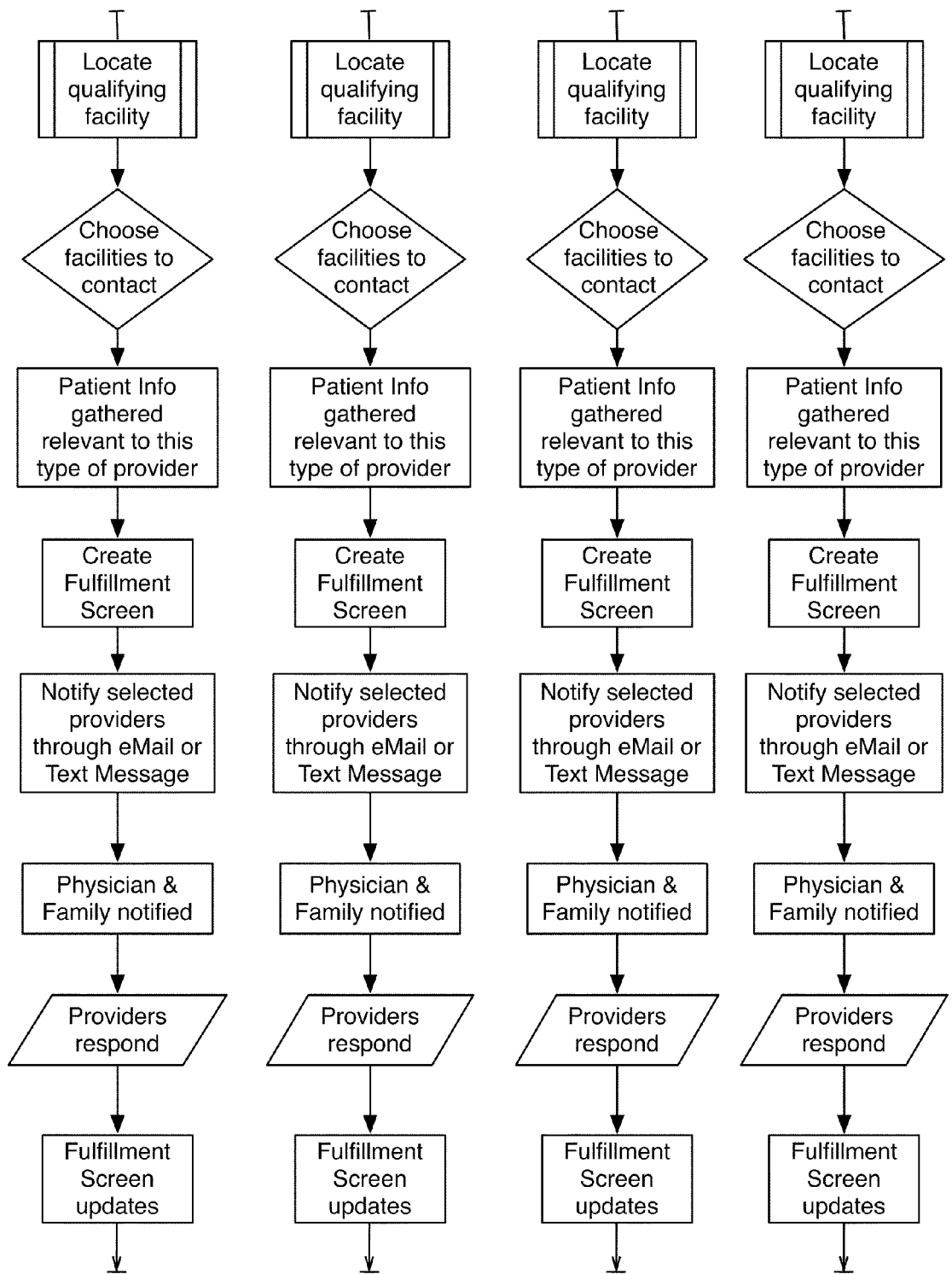
Figures 4, 5:
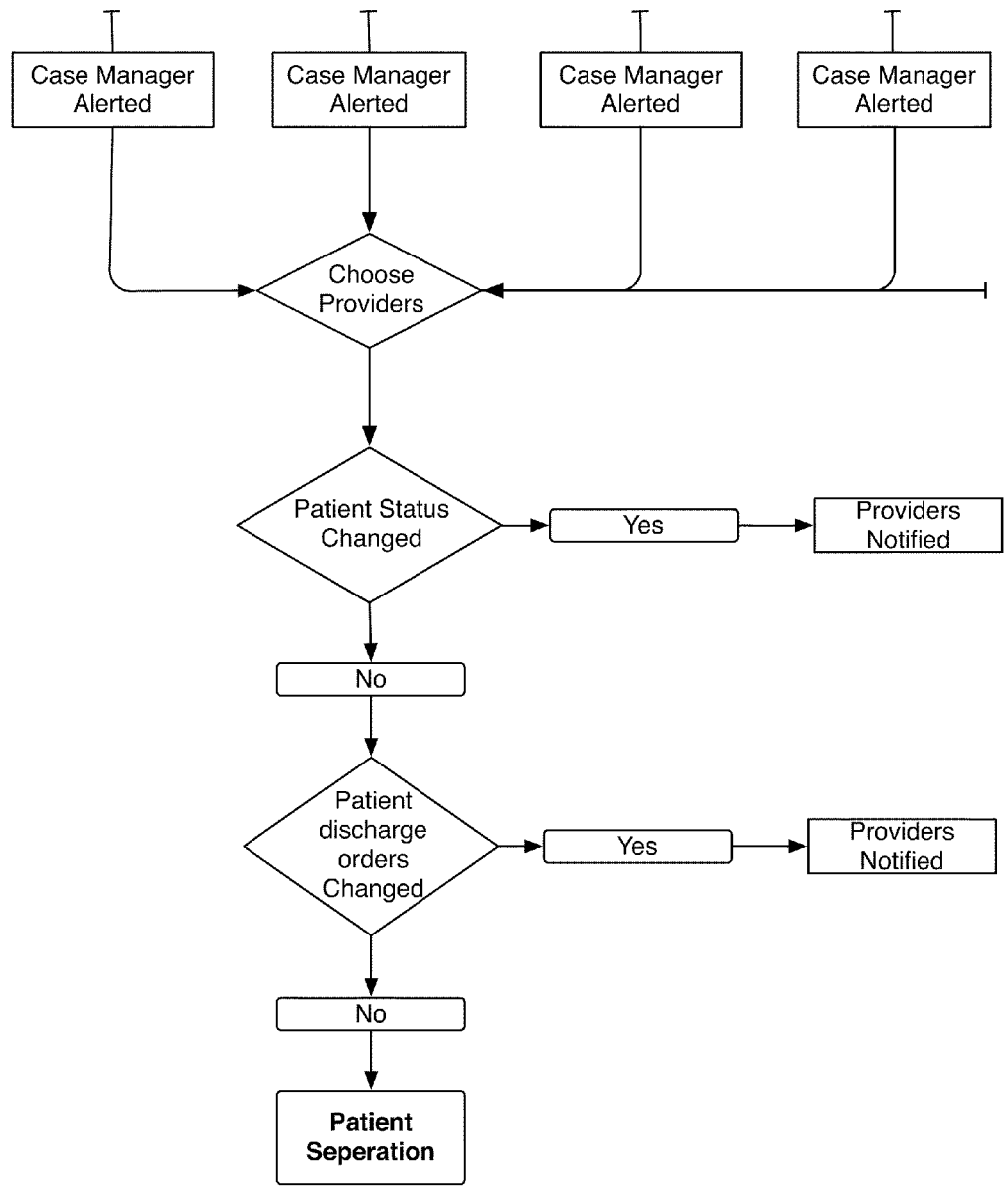
FIG. 5 illustrates another embodiment of a discharge planning process that corresponds to example screen displays that may be provided by the discharge planning system of FIG. 1 or 2.

FIG. 4 illustrates an embodiment of a discharge planning process that may be performed by the discharge planning system 100. FIG. 5 illustrates another embodiment of a discharge planning process that corresponds to example screen displays that may be provided by the discharge planning system 100.

Figures 4, 5, 6:
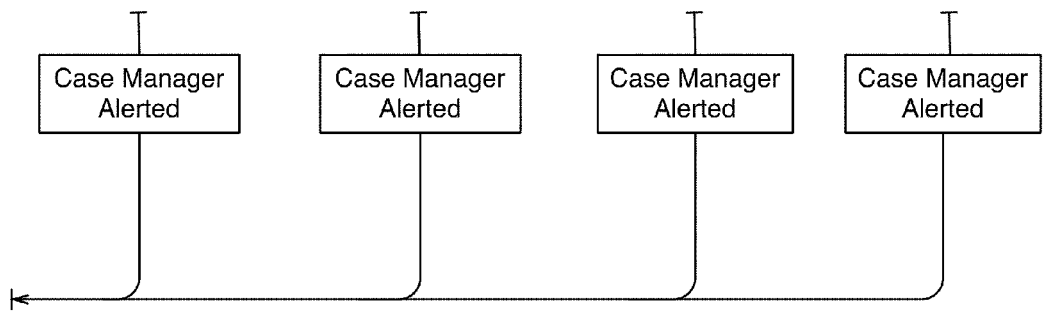
FIG. 6 illustrates another embodiment of a discharge planning process that may be performed by the discharge planning system of FIG. 1 or 2.
Figure 5:
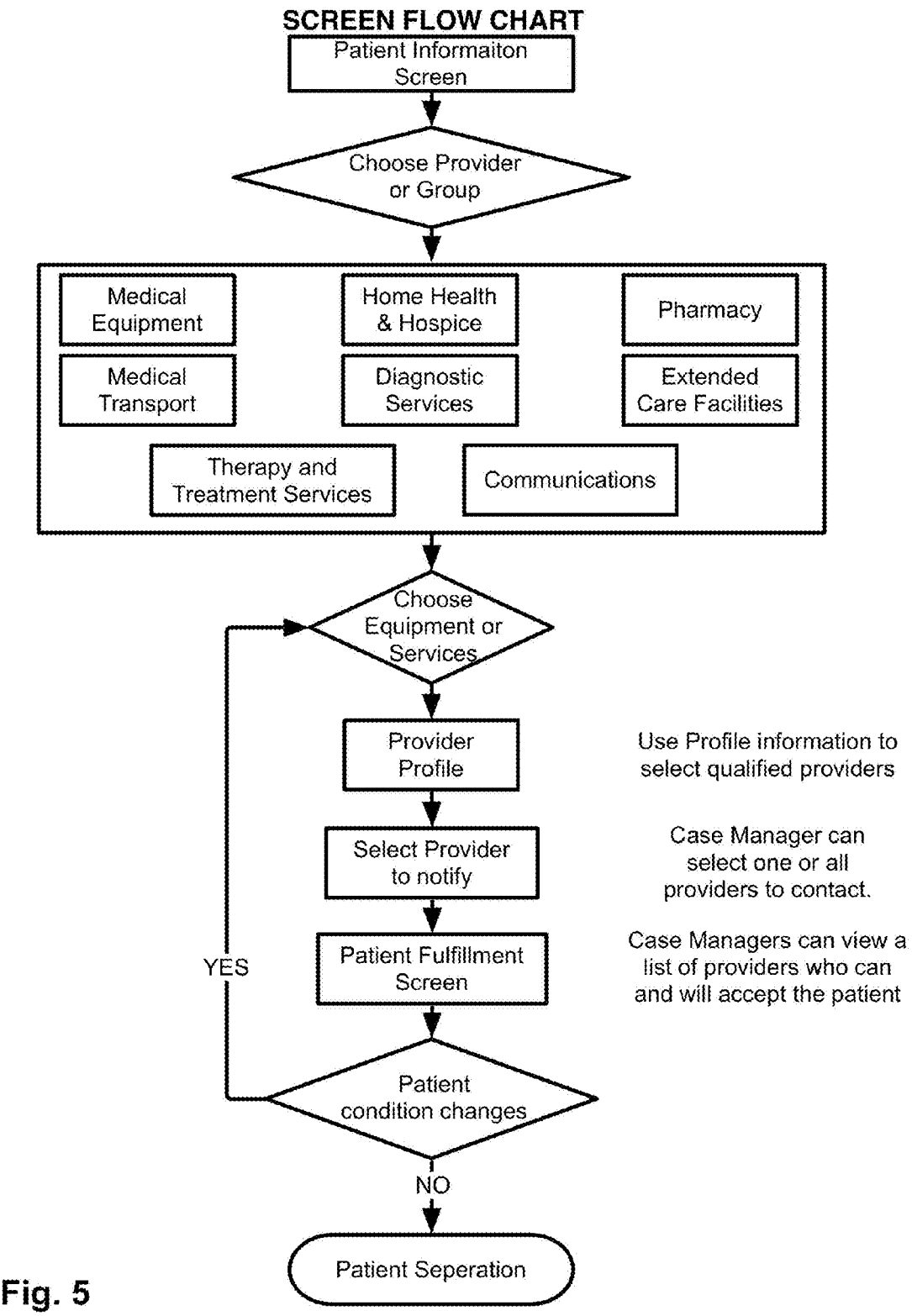
Figures 2, 6:
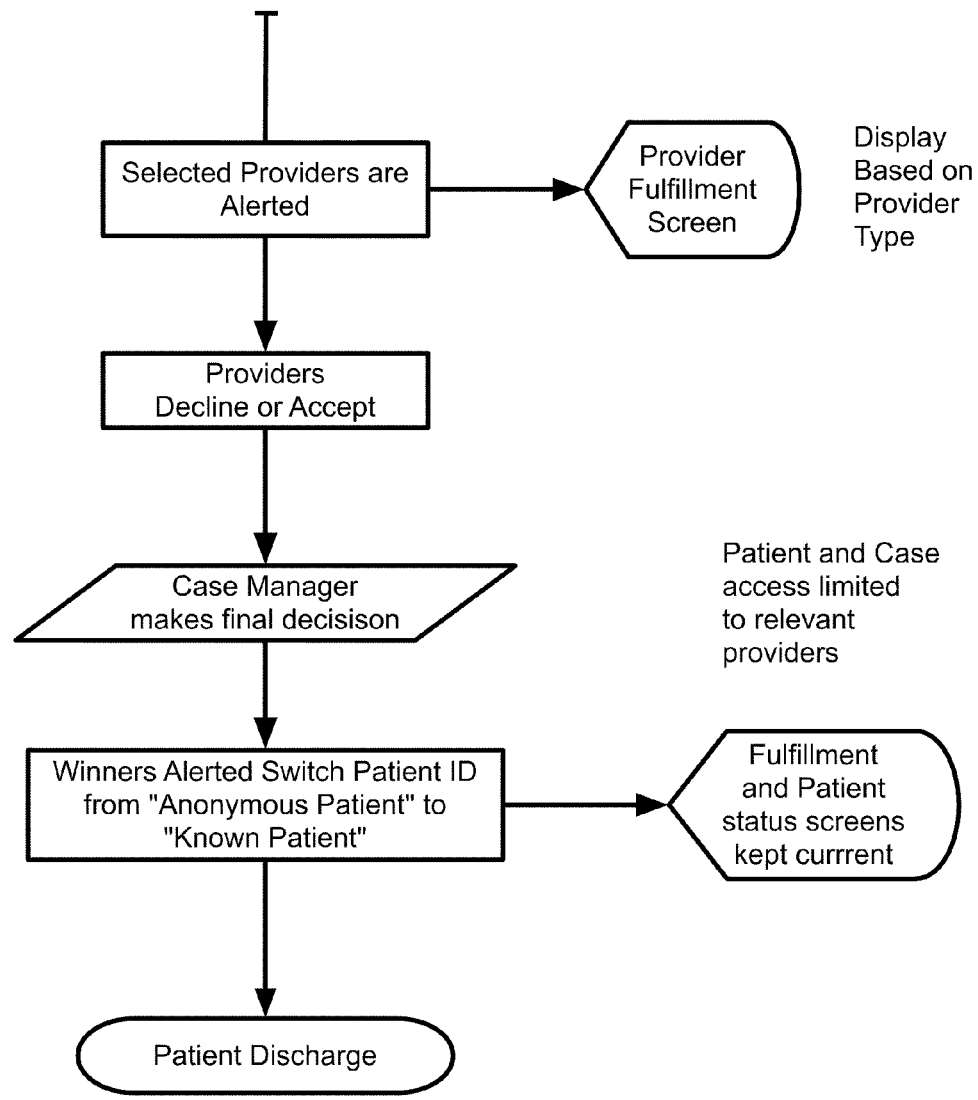

FIG. 6 illustrates another embodiment of a discharge planning process that may be performed by the discharge planning system 100. This is an outline of Interaction of Providers with the System other than the hospital's involvement in the discharge process, we included family interaction at the top. Physician interaction before discharge orders are input into the system. The personnel file holds all the administrative data and relationships to providers. Logged in through provider administration, personnel can interact with the discharge. This diagram simply targets within the discharge timeline where interaction can occur.

FIG. 7 illustrates an example patient fulfillment screen that may be provided by the discharge planning system 100. FIG. 8 illustrates an example patient input screen that may be provided by the discharge planning system 100. Items in the patient input screen include: 200—Patient Information; 210—Patient Advance Directives; 220—Patient Advocates [Family, Friend]; 230—Scheduled Discharge Time; 240—Patient—Vitals, Condition, Status, Diagnosis—not all possible fields shown. 250—Patient Physician(s); 260—Patient Case Manager(s).

FIG. 9 illustrates an example provider display for durable medical equipment that may be provided by the discharge planning system 100. Items in the display include: 400—Patient Information; 410 thru 450—shows the various categories of equipment, and associated services for each.

FIG. 10 illustrates an example provider display for home health and hospice care that may be provided by the discharge planning system 100. Items in the display may include: 500—Patient Information; 510—A list of providers currently on the system; 520 thru 540—shows the various categories of services requested; 550—Report Card feature. Allows those on the system to rank the performance of providers.

Figure 14:
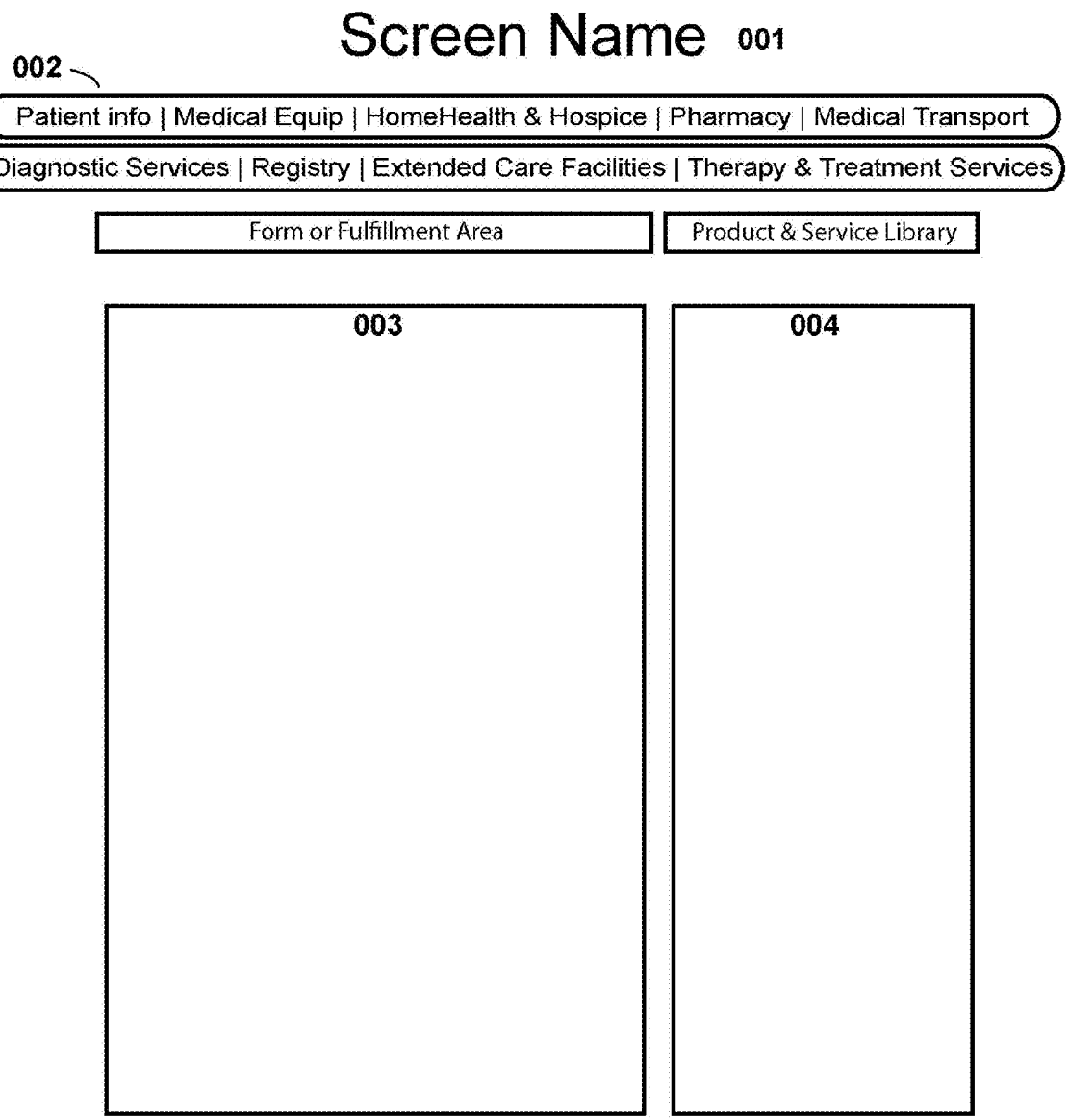
FIG. 14 illustrates a fulfillment screen that may be provided by the discharge planning system of FIG. 1 or 2.

FIG. 11 illustrates an example provider display for pharmacy services that may be provided by the discharge planning system 100. FIG. 12 illustrates an example provider display for diagnostic services that may be performed by the discharge planning system 100. FIG. 13 illustrates an example provider display for extended care that may be provided by the discharge planning system 100. FIG. 14 illustrates a fulfillment screen that may be provided by the discharge planning system 100.

Upstream Booking

One problem some case managers and discharge planners have is finding available beds in extended care facilities, skilled nursing facilities, nursing home and assisted living. Yet those facilities also have trouble filling beds. The problem results from the time required to prepare for patients based on their needs.

Thus, in certain embodiments, the discharge planning system 100 described above includes upstream booking features. Using these features, patients in hospitals and even patients in other facilities like skilled nursing facilities, whose stay can be limited, can be placed on this system with a discharge date days or months in the future. These patients can be monitored and evaluated as candidates to fill beds at other care facilities. The system can automatically update providers in changes in patient condition, diagnosis, or needs. Providers can also use this system to schedule other necessary services for the patient, like treatment or therapies. With these schedules in place, extended care facilities can better fill qualifications for insurance.

Providers on this system may have the ability to place products and services in the Equipment and Care Service database. Bed availability can be part of this system. Like equipment that is listed by part number, with description, with images, as a sale or lease item, beds can be listed by room and bed number, beds can have options associated with them to define ability to fulfill patient needs like Hoyer lift for heavy patients, and skills associated with the facility or by bed like Levin tube and gastrostomy feedings. When providers list bed availability, case managers can see these vacancies offering patients and families a wider variety of choices in care facilities.

At this stage in patient care often co-payment is required, when medicare coverage requirements are met, patients can benefit by full coverage. With advance notice, facilities can increase staff to fulfill qualifications for 'skilled' under Medicare rules. Upstream booking provides a system for patient evaluation, and facility management to help ensure most or all beds are filled, most or all requirements for insurance are met, and patient needs and desires are fulfilled.

Figure 15:
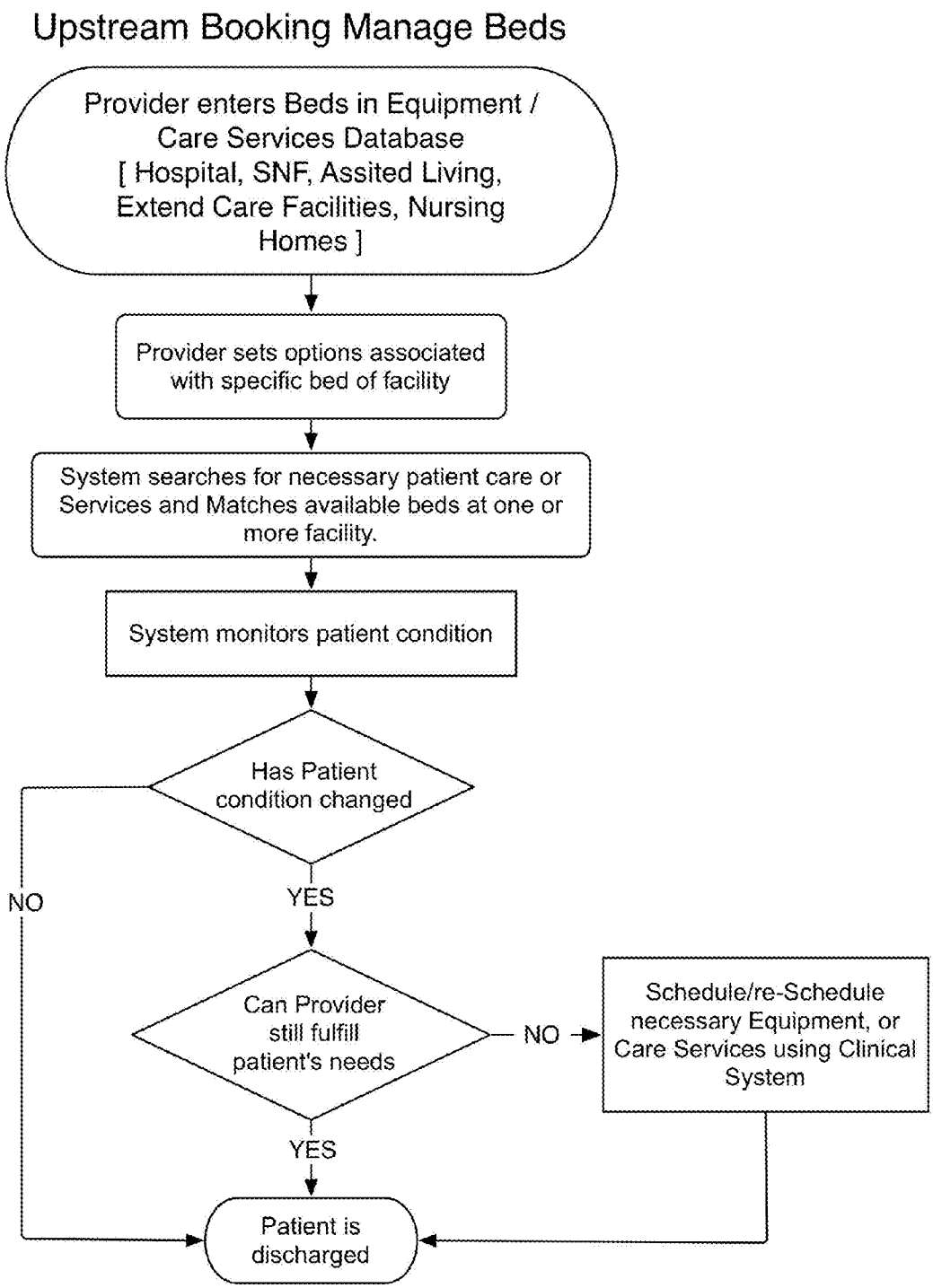
FIG. 15 illustrates an upstream booking process that may be performed at least in part by a provider computer system.

Embodiments of upstream booking are shown in FIG. 15 (providers view, managing beds and options associated with those beds).

CONCLUSION

Depending on the embodiment, certain acts, events, or functions of any of the algorithms described herein can be performed in a different sequence, may be added, merged, or left out all together (e.g., not all described acts or events are necessary for the practice of the algorithm). Moreover, in certain embodiments, acts or events may be performed concurrently, e.g., through multi-threaded processing, interrupt processing, or multiple processors or processor cores, rather than sequentially.

The various illustrative logical blocks, modules, and algorithm steps described in connection with the embodiments disclosed herein may be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various illustrative logical blocks and modules described in connection with the embodiments disclosed herein may be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be a processor, controller, microcontroller, or state machine, combinations of the same, or the like. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated may be made without departing from the spirit of the disclosure. As will be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope. In addition, all trademarks shown and/or described are trademarks of their respective owners.

What is claimed is:

1. A system for electronically managing patient discharges from a medical facility such as a hospital, the system comprising:

a patient data repository comprising physical computer storage configured to store patient data, the patient data including biographical information about a plurality of patients who have been admitted into a medical facility, wherein the patient data repository comprises:
 a first database comprising patient names associated with anonymous identifiers, and
 a second database comprising the patient data associated with the anonymous identifiers, thereby preventing both the patient names and the biographical information of the patients from being compromised should a hacker obtain access to one of the first and second databases;

a provider repository comprising physical computer storage configured to store medical provider data, the medical provider data including information about one or more providers of services to discharged patients, wherein the provider data comprises data regarding the following: durable medical equipment providers, pharmacies, post-discharge care facilities, and medical transportation services; and a discharge planning module comprising computer hardware, the discharge planning module operative to:
 output a discharge planning user interface for presentation to a user, the discharge user interface having functionality for the user to input post-discharge medical care requirements for a medical patient, the post-discharge medical care requirements comprising an insurance used by the medical patient, a desired location of the medical providers, a desired rate for the medical providers, and a desired level of care provided by the medical providers,
 access the provider data in the provider data repository in response to receiving the post-discharge medical care requirements from the user,
 programmatically select, without further user input, medical providers from the provider data who have characteristics in the provider data that match the medical care requirements based at least partly on insurances accepted by the medical providers, locations of the medical providers, rates for the medical providers, and levels of care provided by the medical providers,
 encrypt the discharge request, and
 automatically send the encrypted discharge request to the selected medical providers without further user input and without sending the patient data or the patient name of the medical patient to the selected medical providers, wherein the discharge request comprises four or more of the following:
  a request for the medical patient to stay at a care facility upon discharge,
  a request for prescriptions to be filled upon discharge,
  a request for medical transportation,
  a request for medical equipment to be provided,
  a request for medical care in a home of the medical patient,
  a request for hospice treatment,
  a request for therapy and treatment services, and
  a request for diagnostic services;
 receive acceptances of the discharge request from first ones of the selected medical providers;
 receive a selection of one of the first medical providers that accepted the discharge request;
 in response to said selection, notify the selected first medical provider that the selected first medical provider has been accepted to receive the medical patient and providing the biographical information of the medical patient to the selected first medical provider; and
 update the selected first medical provider to a change in condition of the medical patient, thereby enabling the selected first medical provider to schedule an additional service or equipment for the medical patient;
 wherein the discharge planning module is further configured to provide functionality for each of the one or more providers to update a provider profile with the following items: insurances accepted, equipment provided, services provided, images of products or facilities, and pricing information.

2. The system of claim 1, wherein the discharge planning user interface further provides functionality for the user to input a requested provider response time for responding to the discharge request.

3. The system of claim 1, wherein the discharge planning module is further configured to receive a selection of a second one of the first medical providers in addition to the selected first medical provider, whereby the discharge planning module enables multiple providers to be selected for the medical patient.

* * * * *